(12) United States Patent
Corey et al.

(10) Patent No.: US 6,180,120 B1
(45) Date of Patent: Jan. 30, 2001

(54) COSMETIC SKIN CARE COMPOSITIONS CONTAINING ALPHA HYDROXY ACIDS LINOLEATES

(75) Inventors: Joseph Michael Corey, Waterbury, CT (US); Victor DeFlorio, Cranford, NJ (US); Anthony Vargas, Monroe, CT (US); Stewart Paton Granger, Paramus, NJ (US)

(73) Assignee: Elizabeth Arden Co., division of Conopco, Inc., NY, NY (US)

( * ) Notice: Under 35 U.S.C. 154(b), the term of this patent shall be extended for 0 days.

(21) Appl. No.: 09/206,881

(22) Filed: Dec. 8, 1998

(51) Int. Cl.[7] ................ A61K 6/00; A61K 7/00
(52) U.S. Cl. .............. 424/401; 424/78.02; 514/804; 514/547
(58) Field of Search ............... 424/401, 78.02; 514/804, 547

(56) References Cited

U.S. PATENT DOCUMENTS 5,618,850 * 4/1997 Coury et al. ............... 424/401

* cited by examiner

Primary Examiner—Thurman K. Page
Assistant Examiner—Liliana Di Nola-Baron
(74) Attorney, Agent, or Firm—Radha Masilamani

(57) ABSTRACT

Cosmetic skin care compositions containing alpha hydroxy acid linoleates. The inventive compositions provide, improved oil control and improved skin feel, and/or anti-aging benefits.

4 Claims, No Drawings

COSMETIC SKIN CARE COMPOSITIONS CONTAINING ALPHA HYDROXY ACIDS LINOLEATES

FIELD OF THE INVENTION

Cosmetic methods and compositions for skin care by topical application to the skin of cosmetic compositions containing an alpha hydroxy acid linoleate.

BACKGROUND OF THE INVENTION

Alpha hydroxy acids and esters thereof and linoleic acid esters are well known in the cosmetic art. The compounds employed in the present invention are different at least in that an ester linkage is between the carboxyl group of linoleic acid and the hydroxy group of the hydroxy acid. Alpha carboxylic acids are also known as 2-hydroxy carboxylic acids; thus, the compounds of the present invention may also be called "2-hydroxy carboxylic acid ester of linoleic acid." It has been found, as part of the present invention, that such compounds have a variety of cosmetically beneficial effects on the skin. Specifically, some of these compounds control sebum secretion on the skin, even though, when employed separately, linoleic acid and the hydroxy acid do not achieve the same effect. In addition, alpha hydroxy acid linoleates increase collagen production by skin cells, which is typically associated with skin anti-aging benefits.

SUMMARY OF THE INVENTION

The present invention includes a cosmetic skin care composition comprising:

(a) from 0.0001 to 20 wt. % of 2-hydroxy carboxylic acid ester of linoleic acid of Formula I:

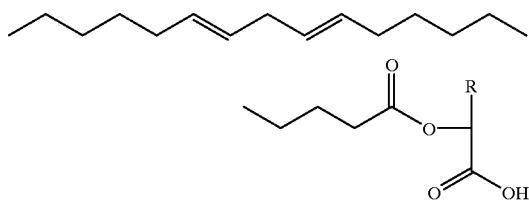

wherein R is a hydrocarbon chain containing from 1 to 20 carbon atoms; and (b) a cosmetically acceptable vehicle.

The inventive compositions provide control of sebum secretion from sebocytes, improved oil control and improved skin feel, prevent shine and stickiness, and provide increased collagen production by skin cells. These effects are associated with reduced appearance of wrinkles and aged skin, improved skin color, treatment of photoaged skin, improvement in skin's radiance and clarity and finish, and an overall healthy and youthful appearance of the skin.

DETAILED DESCRIPTION OF THE INVENTION

Except in the operating and comparative examples, or where otherwise explicitly indicated, all numbers in this description indicating amounts or ratios of material or conditions of reaction, physical properties of materials and/or use are to be understood as modified by the word "about." All amounts are by weight of the final composition, unless otherwise specified.

The term "skin" as used herein includes the skin on the face, neck, chest, back, arms, legs, hands and scalp.

The terms "2-hydroxy carboxylic acid ester of linoleic acid" and "alpha hydroxy carboxylic acid ester of linoleic acid" and "alpha hydroxy carboxylic acid linoleate" and the abbreviation "AHAL" are used interchangeably herein and all refer to the following structural formula:

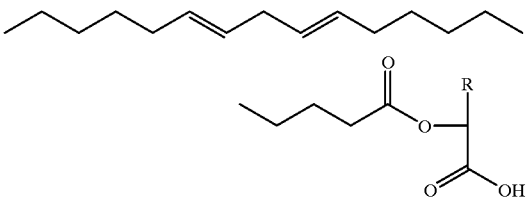

wherein R is a hydrocarbon chain containing from 1 to 20 carbon atoms.

AHAL compounds may be prepared by the following general procedure:

Into a round bottomed flask, alpha hydroxy carboxylic acid is mixed with pyridine (molar ratio in the general range of from 1:1 to 1:2) in an anhydrous, typically non-polar, solvent. Linoleic acid halide, most preferably chloride, is added at a temperature range of 20 to 45° C. The molar range of alpha hydroxy carboxylic acid to linoleic acid halide is typically 1:1 to 1:2. The reaction mixture typically stirs for 2 to 24 hours at a temperature range of 20 to 45° C. The reaction mixture is extracted three times with water before the organic layer is isolated, dried over magnesium sulfate, filtered and concentrated under reduced pressure. Product is purified by column chromatography.

AHAL is incorporated in the inventive compositions in an amount of from 0.0001 to 20%, preferably in order to maximize benefits at a minimum cost, in an amount of from 0.01 to 12%, most preferably from 0.1 to 8%.

Cosmetically Acceptable Vehicle

The composition according to the invention also comprises a cosmetically acceptable vehicle to act as a dilutant, dispersant or carrier for AHAL in the composition, so as to facilitate its distribution when the composition is applied to the skin.

Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 mm$^2$/s (centistokes) at 25° C. Especially desirable are mixtures of low and high viscosity silicones. These silicones are available from the General Electric Company under trademarks Vicasil, SE and SF and from the Dow Corning Company under the 200 and 550 Series, Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the composition, and can, in the absence of other cosmetic adjuncts, form the balance of the composition. Preferably, the vehicle is at least 80 wt. % water, by weight of the vehicle. Preferably, the amount of water is at least 50 wt. % of the inventive composition, most preferably from 60 to 80 wt. %, by weight of the composition. The preferred compositions are oil-in-water emulsions, containing at least 60%, preferably at least 80% water.

Optional Skin Benefit Materials and Cosmetic Adjuncts

The inventive compositions preferably include sunscreens to lower skin's exposure to harmful UV rays.

Sunscreens include those materials commonly employed to block ultraviolet light. Illustrative compounds are the derivatives of PABA, cinnamate and derivatives of salicylate (other than ferulyl salicylate). For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as poly-propylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1% to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Product Use, Form, and Packaging

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

The cosmetic skin conditioning composition of the invention can be formulated as a lotion, a cream or a gel. The composition can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507 (silicone-based anhydrous composition within a gelatine capsule), incorporated by reference herein. The invention accordingly also provides a closed container containing a cosmetically acceptable composition as herein defined.

The following specific examples further illustrate the invention, but the invention is not limited thereto.

EXAMPLE 1

This example illustrates synthesis of lactyl linoleate (lactic acid ester of linoleic acid, R=CH$_3$), a compound included in the inventive compositions.

Methods and Materials:

Proton magnetic resonance spectra were recorded on a Bruker AC 200 model spectrophotometer. Chemical shifts are reported in parts per million from teramethylsilane as an internal standard. Spin multiplicities are indicated as follows: s (singlet), d (doublet), t (triplet), q (quartet), m (multiplet) and br (broad). The deuterated NMR solvents contain 99.0% to 99.8% deuterium in the indicated position, and were purchased from Cambridge Isotopic Laboratories.

Infrared spectra were recorded on a Nicolet Impact model 410 spectrometer using a NaCl cell. Data was processed using Quick IR software. Peak positions are listed in cm-1 as vs (very strong), s (strong), m (medium), w (weak) or br (broad).

Gas chromatography (GC) was performed using a Hewlett-Packard 5890 Series II gas chromatograph with an HP 7673 injector controlled by the Hewlett-Packard ChemStation software. The Hewlett-Packard HP-1 column used was 25 M×0.22 mm with a 0.33 um coating of cross-linked methyl silicone. The parameters were as follows:
Inj. temp.=250° C., det. temp.=250° C., initial oven temp.= 50° C., initial time=5 min., rate=25° C./min., final oven temp.=250° C. Samples were analyzed as trimethyl silyl ethers/esters, Gas chromatography/mass spectrometry was performed on a Hewlett-Packard 5890 Series II gas chromatograph in conjunction with a Finnigan MAT ITD 800 ion trap detector. The 25 M×0.32 mm HP-5 column had a 0.52 um coating of 5% cross-linked phenyl methyl silicone.

Differential Scanning Calorimetry experiments were run on a Dupont DSC with a 2910 cell base and a 2100 thermal analyst. Samples of approximately 1 mg were accurately weighed into aluminum pans which were than hermetically sealed. After equilibration at 30° C., the samples were heated at a rate of 5° C./minute.

All solvents were reagent grade and were used as received. All reagents were purchased from the Aldrich or Sigma Chemical Companies and were used as received.

Into a clean, dry 250 mL round bottomed flask, were charged 1.5 g (16 mmoles) of lactic acid, 50 mLs of dry acetone and 1.3 g (1.3 mmoles) of pyridine. The flask was equipped with a stir bar, addition funnel and nitrogen bubbler. Into the addition funnel were charged 5.0 g (16 mmoles) of linoleoyl chloride in ~20 mLs of acetone. The acid chloride solution was added to the reaction mixture dropwise at room temperature. Upon completion of the addition, the reaction was heated to 35° C. for 30 minutes before being cooled to ambient temperature. The reaction then continued to stir overnight.

The acetone was removed under vacuum and the product was dissolved in ether before being extracted three times with water. The ether layer was dried over magnesium sulfate, filtered and concentrated to give 5.0 g of a clear, pale amber colored liquid. Gas chromatography analysis indicates product is 94% pure.

IR (neat): 1753 cm-1 (s)
$^1$H NMR (200 MHz, CdCl$_3$): d 11.6 (s, 1 H) , 5.2 (m, 4 H), 4.9 (qt, 1 H), 2.7 (t, 2 H), 2.3 (t, 2 H), 1.9 (d,br. 4 H), 1.5 (t, br. 2 H), 1.4 (d, 3 H), 1.2 (br., 14 H), 0.8 (t, 3 H)
GC (Retention time): 16.2 minutes
m/z (GC/MS): 497 (M+H)$^+$ (2×TMS)

EXAMPLE 2

This example illustrates synthesis of "lanolin" linoleate, a compound included in the inventive compositions, "Lanolin" may be obtained from Croda Universal Ltd. (England) and is a name for a mixture of hydroxy acids containing from 14 to 19 carbon atoms and other acids. The specific fatty acid composition of lanolin is as follows, according to the manufacturer's certificate of analysis:

| Lanolin Fatty Acid Composition | |
|---|---|
| Quantified hydroxy acids by internal standards | % w/w |
| iC$_{14}$OH | trace |
| nC$_{14}$OH | 2.4 |
| iC$_{15}$OH | 0.45 |
| nC$_{15}$OH | 1.2 |
| iC$_{16}$OH | 0.85 |
| nC$_{16}$OH | 25.9 |
| nC$_{17}$OH | 0.35 |
| iC$_{18}$OH | 6.2 |
| nC$_{18}$OH | 1.3 |
| nC$_{19}$OH | 0.5 |
| Group Total | 39.15 |
| Hydroxy Acids | 39.1 |
| ISO Acids | 18.9 |
| Anteiso Acids | 20.3 |
| Normal Acids | 14.3 |
| Unknowns | 7.4 |
| Sum of Group Total | 100.0% |

Methods and Materials

Proton magnetic resonance spectra were recorded on a Bruker AC 200 model spectrophotometer. Chemical shifts are reported in parts per million from teramethylsilane as an internal standard. Spin multiplicities are indicated as follows: s (singlet), d (doublet), t (triplet), q (quartet), m (multiplet) and br (broad). The deuterated NMR solvents contain 99.0 to 99.8% deuterium in the indicated position, and were purchased from Cambridge Isotopic Laboratories.

Infrared spectra were recorded on a Nicolet Impact model 410 spectrometer using a NaCl cell. Data was processed using Quick IR software. Peak positions are listed in cm-1 as vs (very strong), s (strong), m (medium), w (weak) or br (broad).

Gas chromatography (GC) was performed using a Hewlett-Packard 5890 Series II gas chromatograph with an HP 7673 injector controlled by the Hewlett-Packard ChemStation software. The Hewlett-Packard HP-1 column used was 25 M×0.22 mm with a 0.33 um coating of cross-linked methyl silicone. The parameters were as follows:
Inj. temp.=250° C., det. temp.=250° C., initial oven temp.=50° C., initial time=5 min., rate=25° C./min., final oven temp.=290° C. Samples were analyzed as trimethyl silyl ethers/esters or methyl esters.

Gas chromatography/mass spectrometry was performed on a Hewlett-Packard 5890 Series II Gas Chromatograph with a carrier gas of helium, 47 mL/min total flow 12 psi constant column headpressure. Column flow rates, ml/min (calculated): 4.59 @ 50° C., 3.60 @ 100° C., 2.40 @ 200° C., 1.76 @ 290° C. Temperatures (° C.): Injector: 290 Transfer line: 300. Oven program: initial 50 (5 min. hold), ramp 25/min to 290 (45 min. hold). Column: Hewlett-Packard fused silica capillary column (HP-5), 5% cross-linked phenyl methyl siloxane, 25 m×0.32 mm ID×0.17 µm film thickness (Serial# 3054-03A-16F)
MS: Finnigan MAT SSQ-710 Single Quadropole Mass Spectrometer. Temperatures (° C.): Source: 150, Manifold: 70, Cl Reagent Gas: NH3, anhydrous, at 5 torr, Electron Source: 200 µA, 70 V for El, 100 V for Cl Mass Range: m/z 40–800 for El, m/z 55–1000 for Cl, Detector: Electron multiplier: 800 V, Electrometer gain: 7, Collision dynode: −15 kV All solvents were reagent grade and were used as received. All reagents were purchased from the Aldrich or Sigma Chemical Companies and were used as received.

Into a clean, dry 250 mL round bottomed flask, were charged 11.7 g (16 mmoles) of Croda Crossential AHA, ~200 mLs of dry methylene chloride and 1.3 g (16 mmoles) of pyridine. The flask was equipped with a stir bar, addition funnel and nitrogen bubbler. Into the addition funnel were charged 5.0 g (16 mmoles) of linoleoyl chloride in ~20 mLs of methylene chloride. The acid chloride solution was added to the reaction mixture dropwise at room temperature. Upon completion of the addition, the reaction stirred at ambient temperature overnight.

The methylene chloride was removed under vacuum and the product was dissolved in ether before being extracted three times with water. The ether layer was dried over magnesium sulfate, filtered and concentrated to give 13.2 g of a cloudy beige colored liquid. Gas chromatography analysis indicates product is 30% pure. Purity was increased to 47% by column chromatography IR (neat): 1753 cm$^{-1}$ (s), 1721 cm$^{-1}$
$^1$ H NMR (200 MHz, CdCl$_3$): d 5.2 (m, 4 H), 4.9 (t, 2 H), 2.6 (t, 2 H), 2.3 (t, 2 H), 1.9 (d,br. 4 H), 1.7 (q, br. 2 H), 1.5 (t, br. 2 H), 1.2 (br., 41 H), 0.8 (t, 3 H)
GC (Retention time): 39 minutes
m/z (GC/MS): (M+NH$_4$) as methyl ester

EXAMPLE 3

This example measured production of procollagen I by fibroblasts in response to treatment with lactyl linoleate (LacL) or lanolin linoleate (LanL).

Collagen is a predominant skin protein. Its synthesis decreases with aging or photodamage. The degradation or destruction of collagen increases the tensile strength of the skin causing wrinkles and laxity. Many studies involving human subjects have shown that collagen type I is decreased with increasing severity of photodamage (See Kligman, A., JAMA, (1969), 210, pp. 2377–2380; Lavker, R., J. Inv Derm., (1979), 73, 79–66; Smith J. et al., J. Inv. Derm., (1962), 39, pp. 347–350; and Shuster, S. et al., Br. J. Dermatol., (1975), 93, pp. 639–643); and some correlation in the histology of wrinkles and reduction in collagen levels in the sun-exposed skin has been reported. See Chen, S.; Kiss, I., J. Inv. Derm., (1992), 98. pp. 248–254. Voorhees and colleagues have supported these findings by showing the restoration of collagen type I in photo-damaged human skin by a topical treatment with tretinoin. See Christopher, E., et al., The New Eng. Jou. of Medicine (1993), 329, pp. 530–535. Procollagen I is a precursor of collagen. Increased production of procollagen I in response to a test compound application is a marker of an increased collagen level.

Procollagen I Staining Protocol for Slot Blot

Neonatal human dermal fibroblasts were purchased from Clonetics Corp., San Diego, Calif. All materials for cell culture were purchased from Life Technologies, N.Y. and used in passages 5–10. Cells were seeded at a density of approximately 10,000/well in the inner 48 wells of a 96-well plate in a medium containing DMEM (Dulbecco's Modified Eagle's Medium), high-glucose supplemented with 2 mM L-glutamine, 10% fetal bovine serum, and antibiotic and antimycotic solutions. Cells were then grown to confluence for 2 days (for LacL experiment) and 1.5 days (for LanL experiment). At confluence, the medium was removed and cells were washed with serum-free DMEM, and each well dosed with 200 µl of a solution of a test compound in serum-free DMEM. Each dosing was replicated in a total of six wells. Test compounds were used at concentrations indicated in Table 1 below. Control did not contain a test compound. After 24 hours, the test compound solution or the control solution was removed and cells redosed with 100 µl of a solution of a test compound in serum-free DMEM. Test compounds were used at concentrations indicated in Table 1 below. After 24 hours, the test compound solution or the control solution was removed and stored over the weekend at 40° C. with protease inhibitor (Aprotinin from Sigma) in a ratio of aprotinin to media of 1:200. The test compound solution was then diluted in DMEM (approximately 20 µl sample in 200 µl DMEM).

Transforming growth factor Beta (TGF) was used as a positive control, at a concentration of 10 ng/mL.

Nitrocellulose membrane and 3 sheets of filter paper were soaked in TRIS buffered saline (TBS, pH 7.3.). BioRad slot blot apparatus (BioRad Labs, Calif.) was set up with 3 sheets filter paper on bottom, membrane on top, and tightened. 100 µl TBS was added per well. Vacuum was used to suck TBS through membrane. The test compound solution or control was vortexed, then 100 µl was loaded per well and gravity filtered. Procollagen from the test solution was bound to the membrane at this point in the procedure. Membrane was removed from the apparatus, excess cut off, and bottom right corner notched for orientation. The membrane was placed in blocking solution (5% milk powder in Dulbecco's phosphate buffered saline) overnight at 4° C., with shaking. The membrane was then incubated for 1.5 hrs at room temperature with 1.5mL Rat Anti-Human Procollagen Amino-Terminal Ab (Chemicon MAB1912) in TBS with 0.1% BSA (ratio of antibody to buffer/BSA was 1:100) in a sealed bag with shaking. The membrane was then removed; washed 3 times for 5 minutes in TBS/0.1% Tween. The membrane was then incubated for 1 hour at room temperature in 2 mL of Biotinylated Anti-Rat Peroxidase-Conjugated Ab (Vector Labs) in TBS with 0.1% BSA (ratio of antibody to buffer/BSA was 1:1000) in a sealed bag with shaking.

The membrane was washed 3 times for 5 minutes in TBS/0.1 % Tween. 3 mL PBS was incubated with 30 µl each of solutions A and B from Vectastain Kit for 30 minutes. The membrane was placed in the resulting solution for 30 minutes in a sealed bag with shaking. The membrane was then removed and washed twice for 5 minutes in TBS/ 0.1% Tween. The membrane was then stained using the following solution:

12.5 mg 3-amino 9-ethyl carbazole (Sigma) 3.125 (approximately) mL DMF (N,N-dimethylformamide, from Sigma) 21.5 mL 0.2 M NaOAc buffer, pH 5.2 12.5 µl $H_2O_2$ The membrane was stained until color developed and the reaction stopped with 2 washes for 10 minutes in tap water. The blot was scanned on a Bio-Rad GS700 Image Analysis densitometer. Fold increase was calculated as a ratio of densitometer reading for cells treated with a test compound over control. p-value was calculated using student's t-test.

The results that were obtained are summarized in Tables 1 and 2.

TABLE 1

| | Densitometer Readings | | | |
|---|---|---|---|---|
| | TGF | LacL 0.05% | LacL 0.005% | LacL 0.0005% |
| Control | | | | |
| 0.534 | 1.065 | 0.171 | 0.888 | 0.507 |
| 0.596 | 0.956 | 0.341 | 1.157 | 0.849 |
| 0.811 | 1.339 | 0.494 | 1.456 | 1.082 |
| 0.761 | 1.258 | 0.355 | 1.37 | 1.261 |
| 0.443 | 0.957 | 0.291 | 1.02 | 0.889 |
| 0.366 | 0.868 | 0.259 | 1.376 | 1.236 |
| Average | | | | |
| 0.585 | 1.074 | 0.3185 | 1.211 | 0.9707 |
| Standard Deviation | | | | |
| 0.175 | 0.1867 | 0.1083 | 0.2262 | 0.2841 |
| p-value vs control | 0.000868 | 0.009899 | 0.000317 | 0.0178 |
| fold increase over control | 1.835 | 0.5443 | 2.070 | 1.659 |

TABLE 2

| | | Densitometer Readings | | | | | |
|---|---|---|---|---|---|---|---|
| Control | TGF | LanL 0.01% | LanL 0.001% | LanL 0.001% | Lanolin 0.01% | Lanolin 0.001% | Lanolin 0.001% |
| 861 | 895 | 469 | 916 | 912 | 848 | 848 | 785 |
| 704 | 784 | 517 | 811 | 882 | 769 | 808 | 727 |
| 829 | 905 | 497 | 1031 | 1125 | 861 | 747 | 760 |
| 843 | 934 | 661 | 1041 | 1037 | 898 | 887 | 827 |
| 783 | 936 | 679 | 1036 | 1051 | 876 | 951 | 805 |
| 765 | 1148 | 775 | 990 | 1150 | 1019 | 1251 | 1044 |
| Average | | | | | | | |
| 798 | 934 | 600 | 971 | 1027 | 879 | 915 | 825 |
| Standard Deviation | | | | | | | |
| 58.5 | 119 | 123 | 91.3 | 109.2 | 81.7 | 178 | 113 |
| p-value vs control | | | | | | | |
| | 0.0305 | 0.005131 | 0.00289 | 0.00111 | 0.0765 | 0.155 | 0.612 |

TABLE 2-continued

Densitometer Readings

| Control | TGF | LanL 0.01% | LanL 0.001% | LanL 0.001% | Lanolin 0.01% | Lanolin 0.001% | Lanolin 0.001% |
|---|---|---|---|---|---|---|---|
| fold increase over control | | | | | | | |
| | 1.17 | 0.752 | 1.217 | 1.287 | 1.10 | 1.15 | 1.03 |

It can be seen from the data in Table 1 that lactyl linoleate at 0.05% and 0.005% significantly increased procollagen I production. Also, the addition of lanolin linoleate (Table 2) at various concentrations to fibroblast cultures resulted in increased procollagen I production, as compared to non-esterified lanolin which did not result in procollagen increase. The results indicate that AHA linoleates significantly increase procollagen I production.

EXAMPLE 4

This example reports an in vitro analysis of sebum suppression by various test compounds. "Oily skin" is an undesirable skin condition which results from the excessive amount of sebum on the skin, Sebum is skin oil which is produced by sebocytes (cells of the sebaceous glands in the skin) and is then secreted to the skin surface. Oily skin is associated with a shiny, undesirable appearance and a disagreeable tactile sensation. Oily skin affects various age groups.

In vitro Sebocyte Lipogenesis Assay

Secondary cultures of human sebocytes (obtained from a male donor) were grown in 48-well tissue culture plates (Costar) in a growth medium consisting of Clonetics Keratinocyte Basal medium supplemented with the following additives: 14 $\mu$g/ml bovine pituitary extract, 0.4 $\mu$g/ml hydrocortisone, 5 ug/ml insulin, 10 ng/ml epidermal growth factor, $1.2 \times 10^{-10}$ M cholera toxin, 100 units/ml penicillin and 100 $\mu$g/ml streptomycin. All sebocytes were incubated at 37° C. in the presence of 7.5% $CO_2$ until three days post-confluence (approximately 7 days). The growth medium was changed every 2 days. Sebocytes grown under these conditions will begin to accumulate intracellular lipid droplets characteristic of sebocytes in vivo.

On the day of experimentation, the growth medium was removed and the sebocytes washed three times with Dulbecco's Modified Eagle's medium (DMEM; phenol red free). Fresh DMEM in 0.5 ml amount was added to each well along with 1 $\mu$l of a test agent (solubilized in ethanol) at final concentrations ranging from 1 micromolar to 1 millimolar. Triplicate wells were utilized for each sample. Controls consisted of DMEM, ethanol, and phenol red, a positive control which decreases sebum production and was used to verify the integrity of the sebocyte assay, Phenol red, lactic acid, linoleic acid, oleic acid, and palmitic acid were all obtained from Sigma. All sebocyte cultures were returned to the incubator for an additional 20 hours.

The following morning, radioactive label was prepared by adding 100 $\mu$l of $^{14}$C labeled acetic acid (Amersham, sodium salt, specific activity of 56 mCi/mmol) to 50 ml of fresh DMEM.

Then, 50 $\mu$l was added to each well containing the sebocytes and test agents. The cultures were returned to the incubator for 4 hours, Thereafter, the sebocytes were rinsed three times with phosphate buffered saline to remove unbound active and radioactive label. Radioactive label remaining in the sebocytes was counted using a Beckman scintillation counter. The results were expressed as % reduction compared to control (ethanol). The higher the number, the better the inhibitory result, p-values were calculated using Lotus 1-2-3 t-test.

The results that were obtained are summarized in Table 3 below.

TABLE 3

| Treatment | % Reduction | Standard Deviation | p-values vs ethanol control |
|---|---|---|---|
| Experiment 1 | | | |
| 10 $\mu$M Lactyl Linoleate | 38.8 | 11.2 | 0.003 |
| 100 $\mu$M Lactyl Linoleate | 69.6 | 5.7 | 0.0001 |
| 1 $\mu$M Lactyl Linoleate | 71.1 | 4.0 | <.0001 |
| Experiment 2 | | | |
| 1 $\mu$M Lactyl Linoleate | 23.7 | 13.9 | 0.018 |
| Experiment 3 | | | |
| 1 $\mu$M Linoleic Acid | 19.3 | 15.2 | 0.096 |
| 10 $\mu$M Linoleic Acid | 15.2 | 8.4 | 0.042 |
| 100 $\mu$M Linoleic Acid | 16.8 | 2.7 | 0.0018 |
| 10 $\mu$M Phenol Red | 45.3 | 4.4 | 0.0001 |
| Experiment 4 | | | |
| 100 $\mu$M Linoleic Acid | 10.1 | 8.1 | 0.12 |
| Experiment 5 | | | |
| 1 $\mu$M Lactic Acid | -2.5 | 6.3 | 0.41 |
| 10 $\mu$M Lactic Acid | 7.2 | 3.5 | 0.29 |
| 100 $\mu$M Lactic Acid | 18.4 | 5.0 | 0.17 |
| 1 $\mu$M Lactic Acid | 18.9 | 2.8 | 0.17 |
| Experiment 6 | | | |
| 1 $\mu$M Palmitic Acid | -7.4 | 8.2 | 0.214 |
| 10 $\mu$M Palmitic Acid | 8.7 | 2.4 | 0.269 |
| 100 $\mu$M Palmitic Acid | 10.3 | 3.7 | 0.018 |
| 1 $\mu$M Oleic Acid | -5.8 | 4.0 | 0.108 |
| 10 $\mu$M Oleic Acid | -2.9 | 6.5 | 0.519 |
| 100 $\mu$M Oleic Acid | 13.0 | 3.2 | 0.006 |

It can be seen from the results in Table 3 that lactyl linoleate was effective at reducing sebum secretion even at a low concentration of 1 $\mu$M in Experiment 2, and was as effective at that concentration than linoleic acid (Experiment 3). However linoleic acid results did not appear to improve with increased concentration (Experiment 3), whereas lactyl linoleic results did (Experiment 1). The comparison of Experiments 1, 3 and 5 also indicates that lactyl linoleate was more effective (over a range of concentrations) than individual lactic and linoleic acids. Experiment 6 indicates that other $C_{18}$ acids (saturated and mono-unsaturated) are not effective, whereas linoleic acid (with double unsaturation) is effective (Experiment 3).

In Experiment 6, 100 $\mu$M dosages were significant due to low standard deviations, but only 10–13% reduction is not considered effective.

EXAMPLE 6

Example 6 illustrates topical compositions according to the present invention. The compositions can be processed in conventional manner. They are suitable for cosmetic use. In particular the compositions are suitable for application to oily, wrinkled, rough, flaky, aged and/or UV-damaged skin and/or oily skin to improve the appearance and the feel thereof as well as for application to healthy skin to prevent or retard deterioration thereof.

| INGREDIENT | % w/w |
|---|---|
| OIL-IN-WATER EMULSION | |
| DI Water | 73.40 |
| Carbomer | 0.30 |
| Disodium EDTA | 0.10 |
| Glycerin | 3.00 |
| Polysorbate 20 | 2.50 |
| Butylene Glycol | 2.00 |
| Methylparaben | 0.30 |
| Triethanolamine 99% | 0.30 |
| Lactyl Linoleate | 8.00 |
| Isopropyl Myristate | 5.00 |
| Octyl Palmitate | 3.00 |
| Cetyl Alcohol | 1.00 |
| Dimethicone, 100 cst | 0.50 |
| Beeswax | 0.30 |
| Propylparaben | 0.10 |
| Germall II | 0.10 |
| Fragrance | 0.10 |
| Total → | 100.00 |
| OIL-IN-WATER EMULSION | |
| DI Water | 71.20 |
| Xanthan Gum | 0.20 |
| Disodium EDTA | 0.10 |
| Glycerin | 5.00 |
| Butylene Glycol | 2.00 |
| Methylparaben | 0.30 |
| Lanolin Linoleate | 5.00 |
| Isopropyl Myristate | 5.00 |
| Octyl Palmitate | 3.00 |
| Cetyl Alcohol | 1.00 |
| Dimethicone, 100 cst | 0.50 |
| Steareth-2 | 0.40 |
| Steareth-21 | 3.00 |
| Propylparaben | 0.10 |
| Germall II | 0.10 |
| Fragrance | 0.10 |
| Total → | 100.00 |
| WATER-IN-OIL EMULSION | |
| DI Water | 63.30 |
| Disodium EDTA | 0.10 |
| Glycerin | 3.00 |
| Propylene Glycol | 2.00 |
| Sodium Chloride | 0.70 |
| Methylparaben | 0.30 |
| Cyclomethicone | 14.00 |
| Glycolic acid linoleate | 5.00 |
| Isopropyl Myristate | 5.00 |
| Octyl Palmitate | 3.00 |
| Dimethicone Copolyol | 2.50 |
| Dimethicone, 100 cst | 0.50 |
| Beeswax | 0.30 |
| Propylparaben | 0.10 |
| Germall II | 0.10 |
| Fragrance | 0.10 |
| Total → | 100.00 |
| HYDRO-GEL | |
| DI Water | 82.85 |
| Butylene Glycol | 5.00 |
| PPG-5-Ceteth 20 | 5.00 |
| Glycerin | 3.00 |
| Carbomer | 1.20 |
| Triethanolamine 99% | 1.20 |

| INGREDIENT | % w/w |
|---|---|
| Lanolin linoleate | 1.00 |
| Methylparaben | 0.30 |
| Polysorbate 20 | 0.25 |
| Disodium EDTA | 0.10 |
| Germall II | 0.10 |
| Total → | 100.00 |
| ANHYDROUS SERUM | |
| Cyclomethicone | 72.40 |
| Lactyl Linoleate | 5.00 |
| Isopropyl Myristate | 5.00 |
| Octyl Palmitate | 3.00 |
| Polyglycerol-6 Dioleate | 5.00 |
| Butylene Glycol | 4.00 |
| Dimethicone, 100 cst | 5.00 |
| Beeswax | 0.30 |
| Propylparaben | 0.20 |
| Fragrance | 0.10 |
| Total → | 100.00 |
| HYDRO-ALCOHOLIC GEL | |
| DI Water | 52.85 |
| Alcohol SDA40B | 30.00 |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| Lanolin linoleate | 1.00 |
| Methylparaben | 0.30 |
| Polysorbate 20 | 0.25 |
| Disodium EDTA | 0.10 |
| Germall II | 0.10 |
| Total → | 100.00 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin conditioning composition comprising:
   (a) from about 0.0001 to about 20 wt. % of 2-hydroxy carboxylic acid ester of linoleic acid of Formula I:

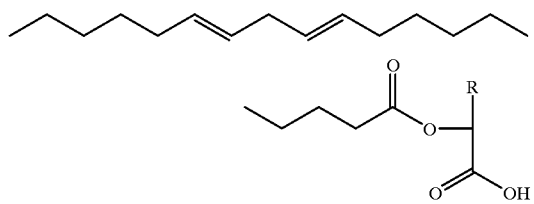

wherein R is a hydrocarbon chain containing from 1 to 20 carbon atoms; and
   (b) a cosmetically acceptable vehicle.

2. The composition of claim 1, wherein R is $CH_3$.

3. The composition of claim 1, wherein R contains from 14 to 20 carbon atoms.

4. A method of reducing or controlling sebum secretion from sebocytes in the skin, the method comprising applying to the skin the composition according to claim 2.

* * * * *